United States Patent [19]

Kapmeyer et al.

[11] 4,305,925

[45] Dec. 15, 1981

[54] LATEX REAGENT

[75] Inventors: Wolfgang Kapmeyer; Axel Sieber, both of Marburg, Fed. Rep. of Germany

[73] Assignee: Behringwerke Aktiengesellschaft, Marburg, Fed. Rep. of Germany

[21] Appl. No.: 146,348

[22] Filed: May 5, 1980

[30] Foreign Application Priority Data

May 7, 1979 [DE] Fed. Rep. of Germany ....... 2918342

[51] Int. Cl.$^3$ ............................................. G01N 33/54
[52] U.S. Cl. ................................... 424/12; 23/230 B; 356/339; 356/340; 424/8; 424/11; 424/13; 424/78; 422/56
[58] Field of Search .................... 23/230 B; 424/8, 11, 424/12, 13, 78; 356/338, 339, 340; 422/55, 56, 105

[56] References Cited

U.S. PATENT DOCUMENTS

| | | | |
|---|---|---|---|
| 3,925,018 | 12/1975 | Saunders | 424/12 X |
| 4,035,316 | 7/1977 | Yen | 424/12 X |
| 4,191,739 | 3/1980 | Uzgiris | 424/12 |

OTHER PUBLICATIONS

Grange et al., J. Immunol. Meth., vol. 18, 1977, pp. 365-375.
Virella et al., J. Immunol. Meth., vol. 22, 1978, pp. 247-251.

*Primary Examiner*—Anna P. Fagelson
*Attorney, Agent, or Firm*—Curtis, Morris & Safford

[57] ABSTRACT

What is disclosed is an improved nephelometric method for detecting an antigen or antibody by contact thereof in a liquid medium with particles of a latex reagent comprising latex particles of different sizes loaded with different amounts of a corresponding antibody or antigen and then measuring the light scattered by a latex reagent.

4 Claims, No Drawings

LATEX REAGENT

The invention relates to a latex reagent, the preparation thereof and its use for detection and determination of clinically relevant proteins and peptides by means of nephelometric and turbidimetric methods. Apart from radio-and enzyme-immunoassays, nephelometric methods are used for determining antigens and antibodies. Light scattering and thus the sensivity of the nephelometric method can be increased by the particle size of the antigen or the antibody. A useful method is to bind the antigen or antibody to latex particles which for their part scatter the light.

As is indicated in the papers of J. Grange et al. in J. Immunol. Meth. 18(1977), 365–375, titration of an antibody bound to a latex with antigen first reduces the stray light signal because the number of particles decreases on increasing agglutination. Subsequently, further increase of antigen concentration increases the aggregate size, so that the stray light intensity is improved until it is reduced again with increasing antigen amount in the antigen excess. For the quantitative test it is important to control the agglutination conditions of the latex in such a manner that, on titration of latex-bound antibodies with antigen or of latex-bound antigens with antibodies, the increase of agglutination within a wide range can be measured as increase of stray light intensity.

An important group of antibodies are the rheumatoid factors, by which there are to be understood anti-immunoglobulins directed against partially modified immunoglobulins of the IgG or IgM series. The rheumatoid factors for their part belong to the immunoglobulin series IgM, IgG and IgA. Test methods for detection of rheumatoid factors are based on agglutination of, for example, erythrocytes or latex particles coated with IgG. These processes allow only a qualitative determination of rheumatoid factor activity, and reading of the results of these agglutination tests is very subjective. The method described by G. Virella et al., J. Immunol. Meth. 22 (1978), 247–251, documents the state of the art.

For this determination of rheumatoid factors, first a screening test has to be made by means of a dilution series of the sera (1:10, 1:50, 1:250, 1:1250). For precise determination, further dilutions of the sera are prepared in order to obtain a measuring value in the linear range of the calibrating plot. This means that the above process is unfit for routine work. The disadvantages reside in an amibiguous course of stray light intensity in the titration, a very narrow measuring range, that is, a sharp incline of the reference curve, and high blank test values of the latex reagent.

Surprisingly, it has now been found that these disadvantages can be overcome by using a latex reagent which contains latex particles within two different size ranges. Such latex particles are furthermore loaded with different amounts of antigens or antibodies. One component of the reagent is a suspension of latex particles having a size of from 0.1 to 0.35, preferably 0.15 to 0.25, $\mu$m, which are loaded with antigen or antibody in an amount about 0.6 to 3.3 times the weight of the latex; 100 to 500 mg, preferably 150 mg, of human IgG per 150 mg of latex. The second component of the reagent is a suspension of latex particles having a size of from 0.5 to 2, preferably 0.5 to 0.8, $\mu$m, such as is on the market for example as latex-rheumatoid factor reagent for the visual agglutination technique. This latex-rheumatoid factor reagent is loaded according to usual methods with antigen or antibody in an amount about 0.1 times the weight of the latex, e.g. with 0.1 mg of IgG per mg of latex. Of course, this second component of the reagent may be specially prepared, as is the first component. The two components are mixed in a volume ratio of about 4:1 to about 1:2, and the mixture of the two individual substances is preferably present in the form of an aqueous suspension optionally containing buffer substances, neutral salts, stabilizers and preserving agents. The suspension is optionally treated with supersonics. Optionally, it is incubated for a period of time, preferably about 1 week at room temperature, which causes readsorption of IgG possibly separated from the latex by supersonic influence. The latex reagent so obtained is distinguished by a wide measuring range. Optionally, it may be processed to a dry powder which may be resuspended for use.

The latex reagent of the invention can be used in nephelometry and turbidimetry as well as in the Particle Counting Immuno Assay (PACIA) for detection and determination of substances such as proteinaceous antigens and haptens, antibodies, virus constituents, cell constituents, enzymes and hormones; use of the latex reagent for determination of plasma proteins is preferred. The latex reagent is especially suitable for the determination of trace proteins which, due to their low concentration in the serum, are difficult to detect by other methods. It is more suitable still for the nephelometric determination of rheumatoid factors, immunocomplexes and pregnancy-specific proteins such as pregnancy-specific $\beta_1$-glycoprotein, pregnancy-associated alpha$_2$-glycoprotein, and human placenta lactogen.

The latex reagent can be used for the determination of proteins and peptides according to kinetic and terminal point methods.

The latex particles can be loaded with proteins by adsorption or covalent bond, for which bond latex derivatives having free carboxyl, amino, aldehyde or epoxy groups, or vicinal hydroxy groups can be used. Furthermore, small peptides such as hormones may be bound to the latex via a carrier protein. Most favorable is the adsorption bond of proteins to latex.

The latices suitable for the preparation of the reagent of the invention may be obtained by polymerization of olefinically unsaturated monomers.

Preferred are styrene copolymers such as styrene/-butadiene copolymers, acrylonitrile/butadiene/styrene copolymers, vinyl acetate/acrylate copolymers or vinyl chloride/acrylate copolymers.

Polystyrene/latex suspensions or emulsions of suitable particle size are furthermore obtained from a number of manufacturers under different trade names, for example Lytron ® latices of Monsanto Company, St. Louis, Mo., Dylex ® latices of Sinclair-Koppers Company, Pittsburgh, Pa., and Dow Latex Particles of Dow Chemical Company, Indianapolis, Ind., as well as acryl polymers such as Acryl ® particles of Colab Laboratories, Inc., Chicago Heights, Ill. (polymethacrylic ester), and Ubatol U-7001 of Stanley Chemical, Cambridge, Mass.

The following Example illustrates the invention.

(1) Preparation of the latex reagent 150 mg of polystyrene latex prepared according to known methods and having a particle size of 0.1 to 0.35 $\mu$m, preferably 0.15 to 0.25 $\mu$m, is suspended at a concentration of 3.8 mg of latex per ml in a buffer of pH 8.2 containing 0.1 M of glycine and 0.17 M of sodium chloride. The batch is agitated for 5 hours at room temperature with 150 mg of human IgG (aggregated for 10 minutes at 60° C.) and 920 mg of human albumin per 150 mg of latex, and then diluted with physiological saline solution containing 2 mg/ml of bovine serum albumin to give 0.5 mg of latex per ml. A latex product heavily loaded with aggregated IgG is thus obtained, which however, is not yet suitable in this state for laser-nephelometric determination.

Furthermore, a commercial latex-rheumatoid factor reagent for the determination of rheumatoid factors according to the visual agglutination technique (Behringwerke) is likewise diluted with physiological saline solution (2 mg/ml of bovine serum albumin) to give 0.5 ml of latex per ml. The latex product heavily loaded with IgG is mixed with the commercial latex-rheumatoid factor reagent in a mixing ratio of 4:1 to 0.5:1, preferably 2:1, and 250 ml portions of the batch are treated with supersonics for 20 seconds. The reagent is then incubated for one week at room temperature and subsequently stored at 4° C.

(2) Nephelometric determination of the rheumatoid factor

A rheumatoid factor reference serum which is a substandard of WHO rheumatoid factor standard and which has a rheumatoid factor activity of 150 IU/ml and the sera to be tested are heated for 30 minutes to 56° C. for inactivation of complement. The reference serum is diluted in a geometric series of from 1:6 to 1:768, which dilutions give rheumatoid factor activity values of from 25 to 0.2 IU/ml. The sera are diluted in a ratio of 1:100. 50 μm of serum or reference serum dilution and 75 μl of the well shaken latex reagent are mixed in cuvettes suitable for laser nephelometry (Sarstedt).

After one hour of incubation time, 100 μl of physiological saline solution of pH 8.1 containing 0.1 M borate are added, and after a further 15 minutes the light scattering is measured in a laser nephelometer.

For evaluation, the volt data obtained for the standard dilutions are plotted in a reference curve on semilogarithmic paper. On the basis of the reference curve the concentration of rheumatoid factor activity in patient sera is determined.

The test as described allows determination of rheumatoid factor activity in a range of from 0.2 to 25 IU/ml for undiluted serum. Dilution of the sera in a ratio of 1:100 allows thus a rheumatoid factor determination in a range of from 20 to 2500 IU/ml of rheumatoid factor activity in the serum, which range is important for the diagnosis of rheumatoid arthritis. The test as described is well reproducible with an intra assay coefficient of variation of 3% and an inter assay coefficient of variation of 7%.

Following the the Example, other antibodies or antigens can be determined.

What is claimed is:

1. In a method for the nephelometric detection and determination of an antigen or antibody by contacting said antigen or antibody in a liquid medium with a latex reagent comprising latex particles loaded with a corresponding antibody or antigen, respectively, and then measuring the light scattering effected by said latex reagent, the improvement wherein said latex reagent comprises latex particles falling within two different size ranges and respectively loaded with different amounts of said corresponding antibody or antigen.

2. A method as in claim 1 wherein said latex reagent comprises a first quantity of particles having a diameter within a first size range from about 0.1 to 0.35 micron, said first quantity of particles being loaded with said corresponding antibody or antigen in an amount from about 0.6 to 3.3 times the weight of said latex reagent, and a second quantity of particles having a diameter between about 0.5 to 2 microns, said second quantity of particles being loaded with said corresponding antibody or antigen in an amount about 0.1 times the weight of said latex reagent.

3. A method as in claim 2 wherein the ratio by weight of said first quantity of particles to said second quantity of particles is from about 4:1 to about 1:2.

4. A method as in claim 1 wherein a rheumatoid factor is determined.

* * * * *